United States Patent
Welker et al.

(10) Patent No.: US 11,326,158 B2
(45) Date of Patent: May 10, 2022

(54) ENRICHMENT OF CELL-FREE DNA FROM A BIOLOGICAL SAMPLE

(71) Applicant: MYRIAD WOMEN'S HEALTH, INC., South San Francisco, CA (US)

(72) Inventors: Noah C. Welker, South San Francisco, CA (US); Clement S. Chu, South San Francisco, CA (US)

(73) Assignee: Myriad Women's Health, Inc., South San Francisco, CA (US)

( * ) Notice: Subject to any disclaimer, the term of this patent is extended or adjusted under 35 U.S.C. 154(b) by 0 days.

(21) Appl. No.: 16/510,365

(22) Filed: Jul. 12, 2019

(65) Prior Publication Data

US 2019/0367905 A1 Dec. 5, 2019

Related U.S. Application Data

(63) Continuation of application No. PCT/US2018/014980, filed on Jan. 24, 2018.

(60) Provisional application No. 62/452,145, filed on Jan. 30, 2017.

(51) Int. Cl.
 *C12Q 1/68* (2018.01)
 *C12N 15/10* (2006.01)
 *C12Q 1/6806* (2018.01)

(52) U.S. Cl.
 CPC ....... *C12N 15/1013* (2013.01); *C12Q 1/6806* (2013.01)

(58) Field of Classification Search
 None
 See application file for complete search history.

(56) References Cited

U.S. PATENT DOCUMENTS

| | | | |
|---|---|---|---|
| 5,705,628 A | 1/1998 | Hawkins | |
| 6,465,639 B1* | 10/2002 | van Gemen | C12Q 1/6806 536/25.4 |
| 10,640,808 B2* | 5/2020 | Gundling | C12N 15/1003 |
| 2011/0130558 A1* | 6/2011 | Ritt | C12N 15/1006 536/25.4 |
| 2015/0275198 A1* | 10/2015 | Umansky | C12N 15/101 536/25.41 |
| 2017/0016048 A1 | 1/2017 | Blauwkamp | |

OTHER PUBLICATIONS

Outinen et al. Plasma Cell-Free DNA Levels Are Elevated in Acute Puumala Hantavirus Infection. PLoS ONE; 2012; 7(2): e31455: p. 1-7. (Year: 2012).*
"Magnetic DNA Purification: History and recent developments", sepmag, 2015 (8 pages).
Tan et al., "DNA, RNA, and Protein Extraction: The Past and The Present.", Journal of Biomedicine and Biotechnology, 2009, 2009:574398. doi: 10.1155/2009/574398.
Saiyed e tal., "Application of magnetic particles (Fe3O4) for isolation of genomic DNA from mammalian cells", Anal Biochem., Sep. 15, 2006;356(2):306-8. doi: 10.1016/j.ab.2006.06.027. Epub Jul. 7, 2006.
International Search Report issued in PCT/US18/14980 dated Apr. 13, 2018 (3 pages).
Written Opinion issued in PCT/US18/14980 dated Apr. 13, 2018 (8 pages).

* cited by examiner

*Primary Examiner* — Dave T Nguyen
*Assistant Examiner* — Wahwah T Johnson
(74) *Attorney, Agent, or Firm* — Foley & Lardner LLP

(57) ABSTRACT

Provided are methods and compositions for enriching cfDNA fragments from a biological fluid sample. A biological fluid sample, such as a urine sample, is collected and, in certain examples, pretreated before enrichment of the cfDNA. For the pretreatment, the sample is centrifuged to remove large cells and large cellular debris. As part of the pretreatment, the sample is also cleared of additional large cellular debris and excess volume by subjecting the sample to anion exchange chromatography and eluting bound DNA. Following any pretreatment of the sample, different concentrations an alcoholic solution are used—along with a mixture of DNA-binding particles and a chaotropic agent—to enrich the sample with cfDNA fragments having different sizes. For example, a biological sample can be enriched with small cfDNA fragments less than about 100 base pairs in length or large cfDNA fragments greater than about 100 base pairs in length.

19 Claims, 4 Drawing Sheets

SILICA BEAD PURIFICATION
(SMALL SIZE SELECTION)

TO 1 VOLUME OF ELUATE ADD:
-4 VOLUMES BEAD BINDING SOLUTION
-INCUBATE AT ROOM TEMP 10min

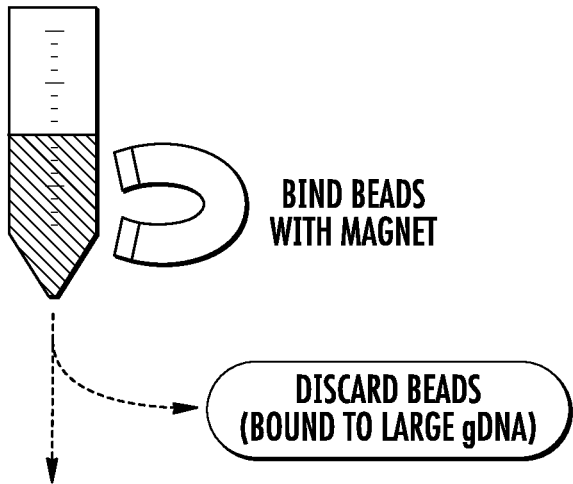

BIND BEADS WITH MAGNET

DISCARD BEADS (BOUND TO LARGE gDNA)

TO SUPERNATANT ADD:
-3 VOLUMES OF 100% ISOPROPANOL
-ADDITIONAL SILANOL BEADS
-INCUBATE AT ROOM TEMP 10min

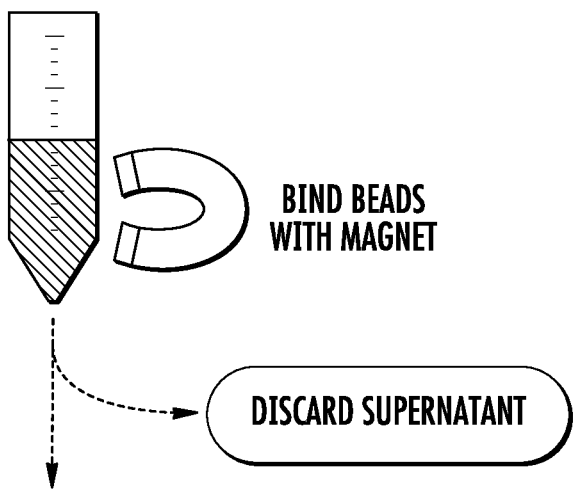

BIND BEADS WITH MAGNET

DISCARD SUPERNATANT

ELUTE "SMALL" CIRCULATING FREE DNA
WITH AQUEOUS SOLUTION

*FIG. 3*

ENRICHMENT OF CELL-FREE DNA FROM A BIOLOGICAL SAMPLE

CROSS-REFERENCE TO RELATED APPLICATION

This application is a continuation of International Patent Application No. PCT/US2018/014980, filed Jan. 24, 2018, which claims priority benefit to U.S. Provisional Application No. 62/452,145, filed Jan. 30, 2017, which is titled "ENRICHMENT OF CELL-FREE DNA FROM A BIOLOGICAL SAMPLE." The entire disclosure of the above-identified priority application is hereby fully incorporated herein by reference.

TECHNICAL FIELD

The present disclosure relates generally to enrichment of cell-free DNA (cfDNA) from a biological sample, and more particularly to methods and compositions for enriching cfDNA of different size ranges from a biological fluid sample.

BACKGROUND

Genetic testing has become an important tool for the early detection of genetic disorders that can lead to patient morbidity and mortality. Specific genetic markers, for example, can be used in several medial applications, from prenatal screenings to the detection of certain genes that are associated with cancer.

Despite the many benefits of genetic testing, conventional methods for collecting genetic material from a patient have remained largely invasive. For example, prenatal screening for genetic abnormalities typically relies on amniocentesis, a procedure that is associated with a risk of miscarriage and/or needle damage to the developing fetus. Other collection methods, such as those used for cancer screenings, typically involve tissue biopsies or drawing blood from the patient, both of which require patient access to medical personnel to collect the sample. Other methods for collecting genetic material include collection of a saliva or stool sample, which is usually performed by the patient and is hence prone to patient error during the collection procedure and patient non-compliance.

One avenue for addressing the challenges associated with collecting genetic material from a patient is the use of circulating, cell-free DNA (cfDNA). For example, cfDNA from a fetus can be obtained from the mother's blood, thus potentially obviating the need for amniocentesis for certain genetic tests. Further, cfDNA that is collected from a patient's blood can be used to obtain information about distant tumors in the patient's body.

While promising, one drawback of using cfDNA is that cfDNA fragments are relatively scarce in the patient's circulation. Hence, a large sample volume, such as a large volume of blood, is needed to obtain enough cfDNA to perform a genetic test. Such large collections are often impractical and put the patient at risk. Further, analyzing cfDNA from blood may miss cfDNA that arises within the urinary tract, as such urinary tract cfDNA is excreted with the urine. Hence, analysis of circulating cfDNA may miss cancers, for example, that arise within the urinary tract. As such, methods and compositions for collecting cfDNA are needed that are less invasive and that do not require large biological sample sizes. Also needed are methods and compositions that enrich cfDNAs arising from the urinary tract.

SUMMARY

In certain example aspects, provided are methods for enriching cfDNA from a biological fluid sample. The method includes, for example, contacting a biological fluid sample with an alcoholic solution, a chaotropic agent, and a plurality of DNA-binding particles to form a reaction solution. The alcohol in the reaction solution has a concentration, for example, of at least 45% v/v. The method also includes separating the plurality of DNA-binding particles from the reaction solution, thereby forming a particle fraction and a non-particle fraction from the reaction solution. Elution of the cfDNA fragments from the plurality of DNA-binding particles of the particle fraction results in an eluate that is enriched with cfDNA fragments having a length of at least about 100 base pairs, such as greater than about 150 base pairs. In certain example aspects, the eluate is enriched with cfDNA from the urinary tract.

In certain other example aspects, provided are methods and compositions for enriching cfDNA, such as small cfDNA fragments, from a biological fluid sample. The method includes, for example, contacting a biological fluid sample with a first alcoholic solution, a first chaotropic agent, and a first plurality of DNA-binding particles, to form a first reaction solution. The alcohol in the first reaction solution has a concentration, for example, of less than about 35% v/v alcohol. The first plurality of DNA-binding particles is then separated from the first reaction solution to form a first particle fraction and a first non-particle fraction. The method further includes contacting the first non-particle fraction with a second alcoholic solution, an optional second chaotropic agent, and a second plurality of DNA-binding particles to form a second reaction solution. The alcohol in the second reaction solution has a concentration, for example, that is greater than about 45% v/v alcohol. The second plurality of DNA-binding particles is then separated from the second reaction solution to form a second particle fraction and a second non-particle fraction from the second reaction solution. Elution of the cfDNA fragments from the second plurality of DNA-binding particles of the second particle fraction yields an eluate that is enriched with cfDNA fragments having a length of less than about 100 base pairs, such as about 10 base pairs and 80 base pairs.

In certain example aspects, the alcohol of the alcoholic solution used to enrich small or large cfDNA fragments is isopropyl alcohol or ethyl alcohol. In certain example aspects, the DNA binding particles are silica particles, such as silica magnetic bead particles. Separating the silica magnetic bead particles from a reaction solution, for example, involves subjecting the silica magnetic bead particles to a magnetic field.

In certain example aspects, provided are compositions for enriching cfDNA from a biological fluid sample. The compositions include an alcoholic solution, a chaotropic agent, and a plurality of DNA-binding particles. In certain example aspects, the concentration of the alcohol in the composition is high, such as greater than about 60% v/v of the composition. In certain other example aspects, the concentration of the alcohol in the composition is low, such as less than about 40% v/v of the composition. In certain example aspects, the alcohol is isopropyl alcohol or ethyl alcohol. In certain example aspects, the DNA-binding particles of the composition are silica bead particles, such as silica magnetic bead particles.

These and other aspects, objects, features and advantages of the example embodiments will become apparent to those having ordinary skill in the art upon consideration of the following detailed description of illustrated example embodiments.

BRIEF DESCRIPTION OF THE DRAWINGS

FIG. 3 is an illustration depicting a method for enriching small cfDNA fragments from a urine sample, in accordance with certain example embodiments.

DETAILED DESCRIPTION OF EXAMPLE EMBODIMENTS

Figure 1:
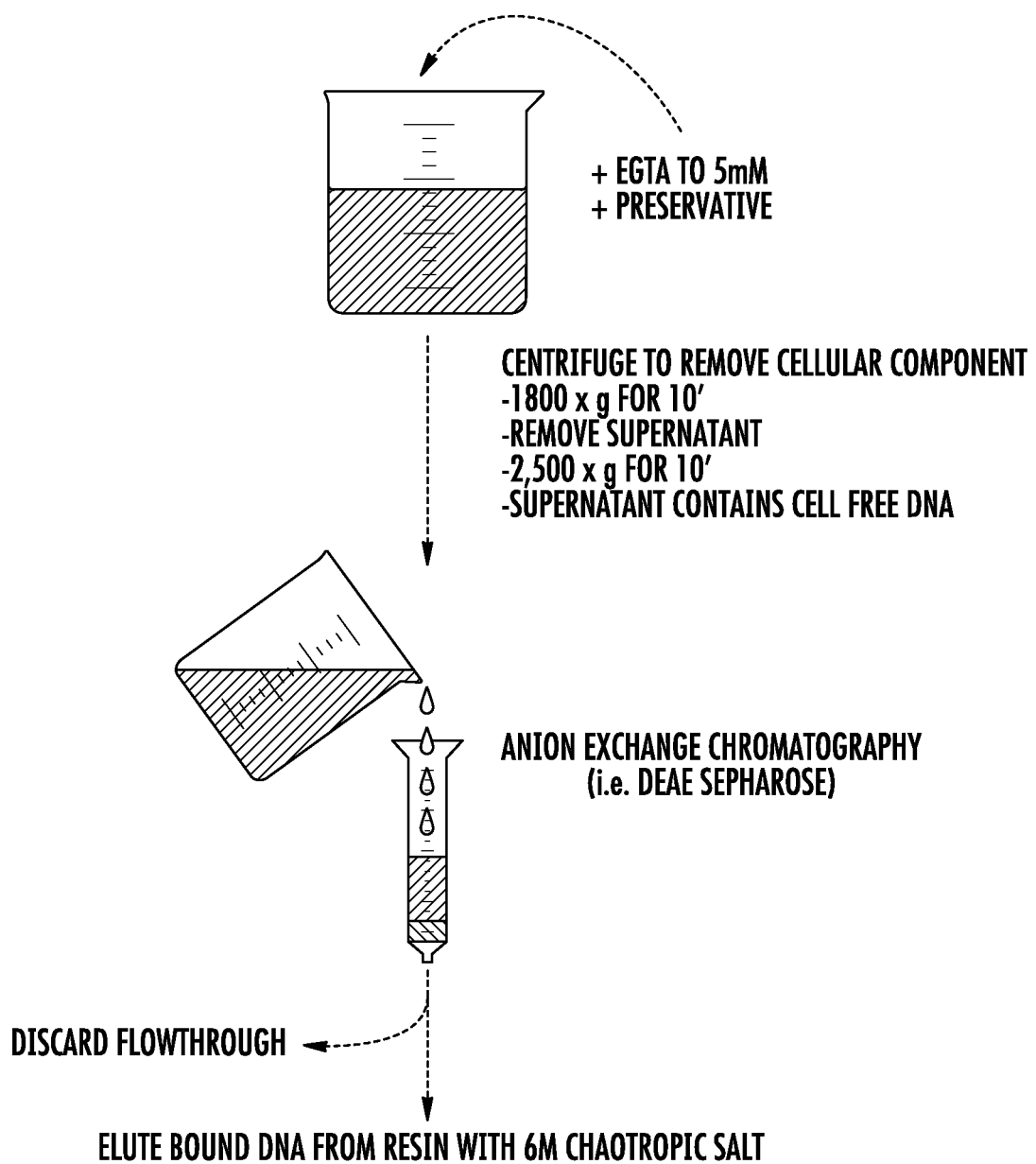
FIG. 1 is an illustration depicting a method for pretreating a urine sample with centrifugation and anion-exchange chromatography, in accordance with certain example embodiments.

The embodiments described herein can be understood more readily by reference to the following detailed description, examples, and claims, and their previous and following description. Before the present system, devices, compositions and/or methods are disclosed and described, it is to be understood that the embodiments described herein are not limited to the specific systems, devices, and/or compositions methods disclosed unless otherwise specified, as such can, of course, vary. It is also to be understood that the terminology used herein is for the purpose of describing particular aspects only and is not intended to be limiting.

Further, the following description is provided as an enabling teaching of the various embodiments in their best, currently known aspect. Those skilled in the relevant art will recognize that many changes can be made to the aspects described, while still obtaining the beneficial results of this disclosure. It will also be apparent that some of the desired benefits of the present invention can be obtained by selecting some of the features of the various embodiments without utilizing other features. Accordingly, those who work in the art will recognize that many modifications and adaptations to the various embodiments described herein are possible and can even be desirable in certain circumstances and are a part of the present disclosure. Thus, the following description is provided as illustrative of the principles of the embodiments described herein and not in limitation thereof.

Overview

Provided herein are methods and compositions for enriching cfDNA from a biological fluid sample. A biological fluid sample, such as a urine sample, is collected and, in certain examples, pretreated before further enrichment of the cfDNA. For the pretreatment, the sample is centrifuged to remove large cells and large cellular debris. As part of the pretreatment, the sample is also cleared of additional large cellular debris and excess volume by subjecting the sample to anion exchange chromatography and eluting bound DNA. Following any pretreatment of the biological sample, for example, specific amounts of an alcoholic solution are used—along with a mixture of DNA-binding particles and a chaotropic agent—to enrich the sample with cfDNA fragments having different sizes.

More particularly, after a biological fluid sample is collected, in certain examples the sample is prepared for centrifugation. A conventional preservative can be added to keep whole cells, such as epithelial cells, intact within the sample solution. Without wishing to be bound by any particular theory, it is believed that the preservative keeps whole cells in the sample from lysing and releasing their genomic DNA in to the sample, thus contaminating the sample with genomic DNA. Because a urine sample, for example, can contain large amounts of salt, such as calcium, a chelator can also be added in certain examples. The sample is then centrifuged to remove the whole cells and large cellular debris, while retaining the cfDNA in the supernatant.

As part of the sample pretreatment, in certain examples the sample is also subjected to anion exchange chromatography. For example, DEAE sepharose chromatography can be used to remove proteins, residual cellular debris, and small molecules that are passed through the column and hence discarded. Further, anion exchange chromatography provides the added benefit of retaining the cfDNA while reducing the overall volume of the fluid sample (i.e., concentrating the sample). With the lower volume of sample, lower volumes of reagents can be used during the enrichment of cfDNA methods described herein, thus making the downstream isolation procedures more manageable and reducing the amount of required reagents (and hence expense). Anion exchange chromatography is particularly beneficial with a urine sample, for example, as urine is a very dilute sample type.

While the pretreatment steps are beneficial, in certain examples the alcohol-based cfDNA enrichment methods provided herein can be used without pretreating the collected sample. For example, the alcohol-based cfDNA enrichment methods and compositions provided herein can be used with an untreated fluid sample, such as a sample of urine that has not been centrifuged and/or subjected to anion exchange chromatography. In certain examples, the biological fluid sample may be batch pretreated, such as by adding anion exchange resin to the collected sample and then eluting bound DNA from the resin with a high-ionic strength solution.

Following any pretreatment, a given volume of the sample, such as a given volume of the cfDNA fraction eluted from the anion exchange purification, is mixed with one or more specific alcoholic solutions, a chaotropic agent, and one or more mixtures of DNA-binding particles, such as silica particles. Without wishing to be bound by any particular theory, it is believed that the alcohol precipitates the cfDNA from the sample solution, thereby releasing the cfDNA from bound proteins so that it can more readily bind to silanol groups of the silica particles in the presence of the chaotropic agent. Hence, it is believed that the addition of alcohol—and the chaotropic agent—favors the binding of the cfDNA to silica particles, with larger cfDNA fragments binding first to the silica particles followed by binding of smaller cfDNA fragments. As such, it is believed that increased alcohol concentration, in the presence of the chaotropic agent, correlates with increased cfDNA binding to silica particles, and more particularly to larger fragments being the first to bind to the particles.

In certain examples, high alcohol concentrations are used to enrich the sample with large cfDNA fragments. For example, a given volume of the biological fluid sample, such as a given volume of the cfDNA eluate from the anion exchange chromatography, is mixed with an alcoholic solution, a chaotropic agent, and a mixture of DNA-binding particles to form a reaction solution that includes about 45% v/v or more alcohol. The DNA-binding particles, such as magnetic silica beads, are then removed from the high-alcohol reaction solution, such as by subjecting the silica magnetic beads to a magnetic field and discarding the supernatant. The silica magnetic beads, for example, are then mixed with an elution buffer to elute the cfDNA. The eluate from the beads is enriched, for example, with larger cfDNA fragments that are greater than 100 base pairs in length, such as between about 100 base pairs in length to 10,000 base pairs.

Without wishing to be bound by any particular theory, it is believed that the larger cfDNA fragments enriched from a urine sample are predominantly post-glomerular cfDNA fragments. That is, it is believed that the larger cfDNA fragments enriched using high alcohol concentrations as described herein are enriched with cfDNA that arises from within the urinary tract. For example, the effective pore of the urinary tract glomerular filtration barrier is around 8 nm, and the membranes of the barrier are generally negatively charged. Hence, cfDNA of larger sizes circulating in the blood plasma are not believed to pass through the glomerular pore—at least to any significant extent. As such, the larger cfDNA enriched from a urine sample via the use of high alcohol is believed to predominantly originate within the urinary tract itself, such as from epithelial cells lining the urinary tract—rather than from non-urinary tract cells.

In certain examples, a low concentration of alcohol is followed by a second, high alcohol concentration to enrich small cfDNA from a biological fluid sample. For example, a given volume of the cfDNA eluate from the anion exchange chromatography pretreatment is initially mixed with an alcoholic solution having a lower amount of alcohol, a chaotropic agent, and a mixture of DNA-binding particles, such as silica magnetic beads. The resultant reaction solution, for example, has an alcohol concentration of less than about 35% v/v alcohol. After removal of the beads, such as by subjecting the magnetic silica beads to a magnetic field, the beads are discarded. Additionally or alternatively, the silica beads are eluted to obtain large cfDNA fragments of approximately 2,000 to 10,000 base pairs in length.

To enrich the small cfDNA fragments from the biological sample, in certain examples a second alcoholic solution with a high amount of alcohol is added to the supernatant (non-particle fraction) of the low alcohol reaction solution, along with an optional chaotropic agent and a second mixture of DNA-binding particles, such as magnetic silica bead. The resulting second reaction solution, for example, has an alcohol concentration of at least about 45% or more alcohol. The second mixture of DNA-particles particles are then removed from the high-alcohol reaction solution and the supernatant is discarded. For example, silica magnetic beads are removed by subjecting the second reaction solution to a magnetic field. The silica magnetic bead particles are then mixed with a low ionic strength elution buffer to elute the cfDNA. The eluate from the beads is enriched, for example, with smaller cfDNA fragments that are less than about 100 base pairs, such as about from 10 base pairs in length to about 80 based pairs. In certain examples, the eluate is enriched with cfDNA fragments of roughly 30 base pairs in length. Such small cfDNAs are believed to be small enough, for example, to pass through the glomerular filtration barrier. Hence, the small cfDNAs are believed to include both circulating cfDNAs and any small, post-glomerular cfDNAs.

In certain examples, provided are compositions for enriching small and/or large cfDNA fragments. The compositions include, for example, an alcoholic solution, such as an isopropyl alcohol or ethyl alcohol solution. The compositions also include a chaotropic agent, along with DNA-binding particles. For example, the DNA-binding particles can be silica magnetic bead particles that can be subsequently removed from the composition by subjecting the composition to a magnetic field. In certain examples, such as when enriching large cfDNA fragments according to the methods described herein, the concentration of the alcohol composition is high, such as about 60% v/v alcohol. In other examples, such as when enriching small cfDNA fragments according to the methods described herein, the concentration of the alcohol in the composition is low, such as less than about 40% v/v alcohol. In certain examples, the compositions are provided in a kit. For example, each of the components of the compositions can be provided together or separately, with separate components to be combined before use.

By using and relying on the methods and compositions described herein, circulating cfDNAs can be obtained in amounts sufficient to carry out genetic testing, but in a non-invasive way. A patient, for example, need only void urine (which he or she would typically do anyway) into a collection vessel. Further, unlike collection of blood samples, large amounts of urine can be collected without any risk to the patient. And because of the ability to collect large amounts of urine non-invasively, enough urine can be collected so that cfDNA can be obtained in amounts sufficient for genetic testing. In addition, when the biological sample is urine, using and relying on the methods and compositions described herein do not risk missing cfDNA that arises in the urinary tract. The small cfDNA fragments that are enriched from a biological sample as described herein, for example, are inclusive of both urinary tract cfDNA and systemic (circulating) small cfDNAs. With regard to the larger cfDNAs—because these cfDNAs are believed to originate predominantly within the urinary tract—these larger cfDNAs can be used with a multitude of screening applications specific to the urinary tract system.

Summary of Terms & Nomenclature

The invention will now be described in detail by way of reference only using the following definitions and examples. All patents and publications, including all sequences disclosed within such patents and publications, referred to herein are expressly incorporated by reference in their entirety.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

As used herein, the singular forms "a," "an" and "the" include plural referents unless the context clearly dictates otherwise.

Ranges or values can be expressed herein as from "about" one particular value, and/or to "about" another particular value. When such a range is expressed, another aspect includes from the one particular value of the range and/or to the other particular value of the range. It will be further understood that the endpoints of each of the ranges are significant both in relation to the other endpoint, and independently of the other endpoint. Similarly, when values are expressed as approximations, by use of the antecedent "about," it will be understood that the particular value forms another aspect. In certain example embodiments, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about. Further, terms used herein such as "example," "exemplary," or "exemplified," are not meant to show preference, but rather to explain that the aspect discussed thereafter is merely one example of the aspect presented.

As used herein, the following abbreviations apply: eq (equivalents); M (Molar); µM (micromolar); N (Normal); mol (moles); mmol (millimoles); µmol (micromoles); nmol (nanomoles); g (grams); mg (milligrams); kg (kilograms); µg (micrograms); L (liters); ml (milliliters); µl (microliters); cm (centimeters); mm (millimeters); µm (micrometers); nm (nanometers); ° C. (degrees Centigrade); h (hours); min (minutes); sec (seconds); msec (milliseconds).

As used herein, an "alcoholic solution" or "alcohol solution" refers to an aqueous alcoholic mixture including one or more linear, branched, or cyclic organic compound containing on or more hydroxyl groups and wherein further the compound is miscible with water. Specific alcohols include, for example, ethanol, isopropanol (i.e., isopropyl alcohol), and methanol.

As used herein, "biological sample" refers to a sample obtained from a subject, including a sample of biological tissue or fluid origin obtained in vivo or in vitro. Such samples can be from, without limitation, body fluids, organs, tissues, fractions, and cells isolated from a biological subject. Biological samples can also include extracts from a biological sample, such as for example an extract from a biological fluid (e.g., blood or urine).

As used herein, a "biological fluid" or "biological fluid sample" refers to any bodily fluids (e.g., blood, blood plasma, sputum, lavage fluid, cerebrospinal fluid, urine, semen, sweat, tears, saliva, and the like, etc.), as well as solid tissues that have, at least in part, been converted to a fluid form through one or more known protocols or for which a fluid has been extracted. For example, a liquid tissue extract, such as from a biopsy, can be a biological fluid sample. In certain examples, a biological fluid sample is a urine sample collected from a subject. In certain examples, the biological fluid sample is a blood sample collected from a subject. As used herein, the terms "blood," "plasma" and "serum" include fractions or processed portions thereof. Similarly, where a sample is taken from a biopsy, swab, smear, etc., the "sample" encompasses a processed fraction or portion derived from the biopsy, swab, smear, etc.

As used herein, a "DNA-binding particle" refers to any conventional solid-phase material that interacts with, or that has been modified to interact with, a DNA fragment, such as a cfDNA fragment. The solid-phase phase material, for example, is any type of an insoluble, usually rigid material, matrix or stationary phase material that interacts with a DNA, either directly or indirectly, in a reaction solution. In certain example embodiments, the DNA-binding particle is a bead.

As used herein, a "bead" refers to a solid-phase particle of any convenient size, and can have an irregular or regular shape. In certain example embodiments, the surface of the bead is modified to bind DNA, either directly and/or indirectly. For example, the bead can include silanol groups, carboxylic groups, or other groups that facilitate the direct and/or interaction of the bead with DNA. In certain example embodiments, silica beads (and gels) can be functionalized by adding primary amines, thiols, sulfhydryls, propyl, octyl, as well as other derivatives to the hydroxyl group (silanol) attached to silica. The bead can fabricated from any number of known materials, including cellulose, cellulose derivatives, acrylic resins, glass, silica gels, polystyrene, gelatin, polyvinyl pyrrolidone, co-polymers of vinyl and acrylamide, polystyrene cross-linked with divinylbenzene, or the like, polyacrylamides, latex gels, polystyrene, dextran, rubber, silicon, plastics, nitrocellulose, natural sponges, silica gels, controlled pore glass (CPG), metals, cross-linked dextrans (e.g., Sephadex®), agarose gel (Sepharose®), and other solid phase bead supports known to those of skill in the art. In certain example embodiments, the beads can be packed together so as to form a column that can be used with conventional column chromatography.

In certain examples, the beads are magnetic beads, and more particularly paramagnetic beads, meaning that the beads are only magnetic in the presence of magnetic field. As those skilled in the art will appreciate, magnetic particles can be include an iron-oxide core coated with silane. Magnetic particles useful for magnetic DNA purification can be made from synthetic polymers, porous glass, or metallic materials like iron-oxide. The particles can be coated with functional groups or, in certain examples, can be left uncoated. While coated particles bound with carboxylic acid are more efficient at binding DNA, other molecules such as streptavidin or those containing free thiol groups can also be attached to the silane coat. In certain examples, any high yield magnetic particles that do not require a coating may be desired, as the lack of a coating and functional groups can allow for a higher surface area for binding nucleic acid. Additionally, particles without a coating are more responsive to an applied electric field. Examples of magnetic beads include, for example, silica-based magnetic beads or carboxylated magnetic beads. Example silica-based magnetic beads include, for example, Dynabeads™ MyOne™ Silane beads, available from ThermoFisher Scientific™.

As used herein, "cell-free DNA" (or cfDNA) refers to DNA that is not within a cell, i.e., DNA that exits outside of a cell. In certain example embodiments, cfDNA includes DNA that is or was circulating in the blood of a subject. Additionally or alternatively, cfDNA includes DNA that is not within a cells but that is freely present in the urine of the subject. In certain example embodiments, the cfDNA is fetal cfDNA, i.e., DNA that originated from the fetus (not the fetal host) and is not within a cell. In certain example embodiments, cell-free fetal DNA includes fetal DNA circulating in maternal (fetal host) blood. In another example embodiment, cell-free fetal DNA includes fetal DNA that exists outside of a cell, for example a fetal cell.

As used herein, the term "elution" or "eluting" refers generally to the process of extracting one material from another by washing with a solvent to remove adsorbed material from an adsorbent. As an example, elution involves washing of loaded ion-exchange resins to remove captured ions. In certain example embodiments, elution is used to remove DNA that is bound directly and/or indirectly to a DNA-binding particle. The eluate is the product that results from the elution process.

As used herein, a "chaotropic agent" refers generally to substances that, without being bound by any particular theory, are thought to disrupt the three dimensional hydrate shell structure of water. Chaotropic agents are understood to interfere with stabilizing intra-molecular interactions mediated by non-covalent forces, such as hydrogen bonds, Van der Waals forces, and/or hydrophobic effects. With regard to DNA, chaotropic agents are believed to disrupt the stabilizing hydrate shell that forms around DNA in an aqueous solution. Some inorganic, organic, and/or mixed salts can have chaotropic properties. Without wishing to be bound by any particular theory, such salts are thought to act, for example, by shielding charges and preventing the stabilization of salt bridges. Example chaotropic agents include guanidinium salts generally, guanidinium isothiocyanate, guanidinium chloride, urea, alkali salts, and sodium dodecyl sulfate.

As used herein, the term "enriched" refers generally to an aqueous solution in which the concentration of a particular component has been increased relative to its original or previous concentration. For example, a fraction of a biological fluid sample that is enriched with cfDNA has a higher concentration of cfDNA as compared to the concentration of cfDNA in the originally collected, un-fractionated sample. In certain example embodiments, a fraction of a biological sample can be enriched with small cfDNA, meaning that the fraction has a higher concentration of the small cfDNA as compared to the originally collected, un-fractionated sample. In certain example embodiments, a fraction of a biological sample can be enriched with large cfDNA, meaning that the fraction has a higher concentration of the large cfDNA as compared to the originally collected, un-fractionated sample.

As used herein, the term "fraction" refers to a partially purified portion of a biological fluid sample. For example, a biological fluid sample that is contacted with DNA-binding particles, such as silica magnetic beads can, upon removal of the beads, be divided in to a particle fraction that includes the beads and a non-particle fraction. cfDNA my then be eluted from the beads of the particle fraction to provide an eluate that is enriched with cfDNA having a specific size.

As used herein, "genetic marker" refers generally to any gene or short genetic sequence that is known or understood to be associated with a disease condition of a subject. The genetic marker can be a variation (which may arise due to mutation or alteration in the genomic loci) that can be observed. A genetic marker can be a short DNA sequence, such as a sequence surrounding a single base-pair change (single nucleotide polymorphism, SNP), or a long one, like minisatellites. In certain example embodiments, the genetic marker is located within a cfDNA sequence in a biological sample of the maternal host subject. The genetic marker, for example, can be the presence or absence of a gene or short genetic sequence.

As used herein, the term "solution" refers to a homogeneous mixture composed of two or more substances. Some skilled in the art refer to "solution" as being intermingled at the molecular level with neither remaining in solid or particulate form. A reaction solution, for example, is a mixture of components that interact with each other. For example, a solution with alcohol, DNA-binding particles, a chaotropic agent, and biological sample form a reaction a solution in which DNA, such as cfDNA, interact with and bind to the DNA-binding particles, either directly or indirectly.

As used herein, a "subject" refers to an animal, including a vertebrate animal. The vertebrate can be a mammal, for example, a human. In certain examples, the subject can be a human patient. A subject can be a "patient," for example, such as a patient suffering from or suspected of suffering from a disease or condition and can be in need of treatment or diagnosis or can be in need of monitoring for the progression of the disease or condition. The patient can also be in on a treatment therapy that needs to be monitored for efficacy. A mammal refers to any animal classified as a mammal, including, for example, humans, chimpanzees, domestic and farm animals, as well as zoo, sports, or pet animals, such as dogs, cats, cattle, rabbits, horses, sheep, pigs, and so on.

Example Embodiments

Provided are example methods for pretreatment of a biological fluid sample, methods for enriching large cfDNA fragments from a biological fluid sample, and methods for enriching small cfDNA fragments from a biological fluid sample, in accordance with certain example embodiments. Also provided are compositions and kits for enriching cfDNA from a biological fluid sample, along with applications for the use of the methods and compositions.

Collection & Pretreatment of a Biological Fluid Sample (for Subsequent cfDNA Enrichment)

In certain example embodiments, a biological fluid sample, such as a urine sample is collected. The sample can be collected by any conventional means. For example, a blood sample can be taken from one of the superficial veins of a human subject's upper limb. A urine sample, for example, can be obtained by having a subject void urine into a sterile collection vessel. For example, a subject may provide between 200-400 ml of urine for a sample. In certain example embodiments, urine is preferred, as a large volume of urine can be non-invasively collected and hence yield more enriched cfDNA following the enrichment procedures described herein. For example, a subject can void several times in to a larger collection container, over the course of several hours, thus permitting the collection of a large urine volume, such a 500 to 2000 ml of urine.

Following collection of the biological fluid sample, in certain example embodiments, a chelator can be added to the sample (e.g., FIG. 1). For example, when the sample is urine, the sample contains substantial amounts of salts and hence dissociated ions, such as calcium and magnesium. Hence, addition of a chelating agent can reduce the salt load of the collected sample, thereby stabilizing the sample. Any suitable chelating agent or combination of chelating agents can be used in accordance with the pretreatment methods described herein. Specific chelators include, for example, ethylenediaminetetraacetic acid (EDTA), ethylene glycol-bis(3-aminoethyl ether)-N,N,N',N'-tetraacetic acid (EGTA), as well as other conventional chelators.

In certain example embodiments, a conventional preservative can also be added to the collected sample, so as to keep whole cells that may be in the sample from lysing and releasing their contents—including genomic DNA which can contaminate the sample (e.g., FIG. 1). Example preservatives include formalin, formaldehyde, alcohol, and imidazolidinyl urea. Additional examples of potential preservatives include, for example, include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride.

In certain example embodiments, the collected urine or a portion thereof is centrifuged to remove whole cells and other cellular large debris (e.g., FIG. 1). For example, the sample is centrifuged, the supernatant retrained, and the pellet is discarded. The cfDNA remains present in the supernatant. In certain example embodiments, the biological sample is subjected to serial centrifugation. For example, the sample is subjected to a low speed centrifugation, such as about 800, 900, 1000, 1100, 1200, 1300, 1400, 1500, 1600, 1800, 1900, 2000, 2100, or 2200×g for roughly 10 minutes and/or until a pellet forms. The supernatant is then removed. In such examples, the supernatant is then centrifuged again at a higher speed, such as about 2200, 2300, 2400, 2500, 2600, 2700, 2800, 2900, or 3000×g for an additional 10 min and/or until a pellet forms. The supernatant is then collected and, for example, combined with the initial supernatant.

In certain example embodiments, the biological fluid sample, such as a urine sample, is additionally or alternatively subjected to ion-exchange chromatography to further ready the biological sample for cfDNA enrichment (e.g., FIG. 1). As noted above, ion-exchange chromatography has the benefit of removing smaller cellular debris, such as large proteins, lipids, and other sub-cellular organelles. Ion-exchange chromatography also advantageously reduces the overall volume of the sample to a more practical and manageable volume, without any significant loss of cfDNA from the sample. Following centrifugation, for example, a urine sample may be 100, 150, 200, 250 ml, or greater. Ion-exchange chromatography can reduce such volumes down to more manageable volumes, such as to about 3, 4, 5, 6, 7, 8, 9, 10, 11, 12, 13, 14, 15, 16, 17, 18, 19, or 20 ml.

Any type of ion-exchange chromatography that facilitates removal of cellular debris and/or reduction of sample volume can be used in accordance with the methods described herein. In certain example embodiments, anion-exchange chromatography is used. For example, a DEAE Sepharose resin slurry (GE Healthcare™) can be used for anion-exchange chromatography, according to known anion-exchange protocols and/or according to the manufacturer's instructions. DNA, including cfDNA, is then eluted from the resin using one or more conventional elution buffers, such as a salt or pH gradient. In certain example embodiments, the bound DNA is eluted, with a high concentration of a chaotropic agent. For example, the DNA can be eluted with high concentrations of a chaotropic salt, such as about 4M, 5M, 6M, 7M, or 8M guanidine thiocyanate or other chaotropic agent.

In certain example embodiments, the collected sample, such as a urine sample or a portion thereof, is subjected to ion-exchange chromatography without the centrifugation steps. For example, "batch" or whole-sample processing of a urine sample can be used in which an anion-exchange resin, such as DEAE Sepharose resin, is added directly to the collected sample. After the sample is mixed with DEAE sepharose with resin, for example, the resin is collected and its bound contents are eluted and used for cfDNA enrichment according to the methods described herein. In other example embodiments, the collected sample, such as a urine sample or a portion thereof, is subjected to centrifugation only, without the ion-exchange chromatography steps. That is, enrichment of cfDNA according to the methods described herein can occur without centrifugation. And, in certain example embodiments, enrichment of cfDNA according to the methods described herein can occur without either centrifugation or ion-exchange chromatography.

Enrichment of Large cfDNA from a Biological Sample

Figure 2:
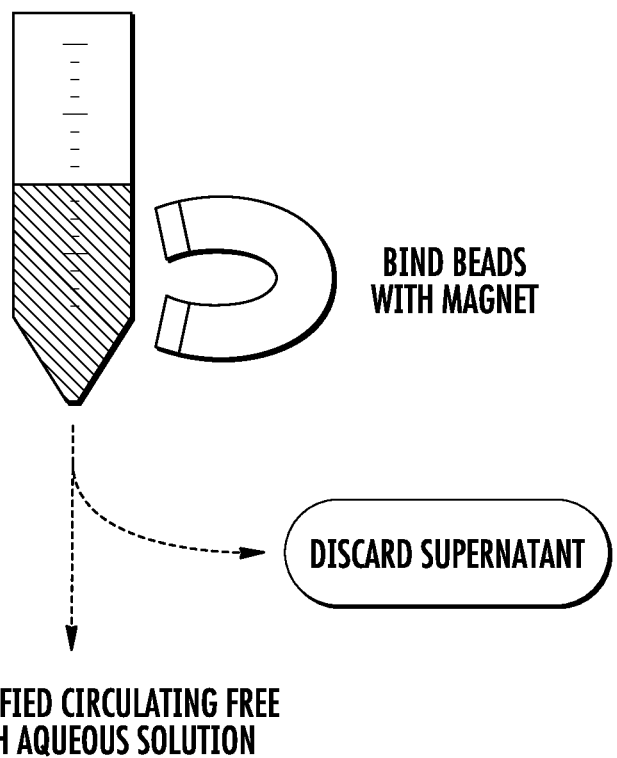
FIG. 2 is an illustration depicting a method for enriching large cfDNA fragments from a urine sample, in accordance with certain example embodiments.

In certain example embodiments, high alcohol concentrations are used—along with a chaotropic agent—to enrich a biological fluid sample with large cfDNA fragments (e.g., FIG. 2). For example, the eluate from one or more of the pretreatment methods is mixed with a high alcohol content alcoholic solution, one or more chaotropic agents, and a mixture of DNA-binding particles to form a reaction solution. In certain example embodiments, other components can also be added to the reaction solution, such as detergents, pH buffers, chelators, etc. Yet because of the addition of the high alcohol content alcoholic solution to the mixture, the resultant reaction solution also has a high alcohol concentration, such as a concentration above 45% v/v alcohol. For example, the reaction solution formed by combining the biological sample eluate, the alcoholic solution, the chaotropic agent, DNA-binding particles, and any other components has an alcohol concentration of 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75% alcohol v/v.

In certain example embodiments, to achieve a high alcohol concentration as described herein, the concentration of the alcohol solution used to form the reaction solution can be high. For example, the alcohol solution that is used to form the reaction solution can be about 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, or 65% v/v alcohol.

In certain example embodiments, to achieve the high alcohol concentration, serial dilutions with an alcohol solution can be used. For example, the sample can be contacted with an initial alcohol solution of 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, or 65% v/v alcohol. Thereafter, a second and/or subsequent alcohol solution of 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, or 65% v/v alcohol can be added. Hence, with single or serial additions of alcohol, the resultant reaction solution has a high alcohol concentration of 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75% alcohol v/v.

With regard to the chaotropic agent of the reaction solution, the chaotropic agent can be any chaotropic agent that favors binding of the cfDNA to the DNA-binding particles. For example, the chaotropic agent can be a chaotropic salt, such as guanidine thiocyanate. In certain example embodiments, such as when the eluate from any pretreatment step contains no chaotropic agent or a lower concentration of chaotropic agent, a higher concentration of the chaotropic agent can be added, along with the other components, to form the reaction solution. For example, the chaotropic agent that is added to form the reaction solution can be chaotropic salt solution, such as a solution of about 4M, 4.5M, 5M, 5.5M, 6M, 6.5M, 7M, 7.5M or 8M guanidine thiocyanate or other chaotropic agent.

In other example embodiments, such as when the eluate from any pretreatment step is eluted with a chaotropic agent—and therefore the eluate already contains a chaotropic agent—a lower concentration of the chaotropic agent can be added, along with the other components described herein, to form the reaction solution. For example, the chaotropic agent that is added to form the reaction solution can be chaotropic salt solution, such as a solution of 0.5M, 1M, 1.5M, 2M, 2.5M, 3M, 3.5M, or 4M guanidine thiocyanate or other chaotropic agent. In certain example embodiments, the final concentration of the chaotropic agent in the reaction solution is about 2M guanidine thiocyanate, such as 0.5M, 1M, 1.5M, 2M, 2.5M, 3M, 3.5M, or 4M guanidine thiocyanate.

The DNA-binding particles of the reaction solution can be any type of DNA-binding particles that bind DNA, including cfDNAs, in the presence of alcohol. For example, the DNA-binding particles can be beads. The DNA-binding particles, such as beads, can thus be used to form the reaction solution having a high alcohol concentration as described herein. In certain example embodiments, the beads can be magnetic beads, such as silica-based magnetic beads, such as magnetic silanol beads. For example, a given amount of the magnetic beads (according to the manufacturer's instructions) can be combined with a solution that includes alcohol and/or a chaotropic agent to form a bead binding solution. The bead binding solution can then be combined with the biological fluid sample—and also combined and/or further adjusted with an alcohol solution, and/or one or more chaotropic agents—to achieve the high-alcohol reaction solution as described herein (e.g., FIG. 2).

To enrich large cfDNA fragments from the biological fluid sample, the reaction solution is incubated for a given amount of time to allow the cfDNA fragments to bind to the DNA-binding particles (e.g., FIG. 2). For example, the reaction solution—which includes, among other components, the biological sample or portion thereof, the chaotropic agent, the DNA-binding particles, and a high concentration of alcohol as described herein—is incubated for 1, 2, 3, 4, 5, 6, 7, 8, 9, 10, 11, 12, 13, 14, 15, 16, 17, 18, 19, or 20 minutes. The reaction solution is incubated, for example, at room temperature, such as at about 20° C., 21° C., 22° C., 23° C., 24° C., or 25° C. In other example embodiments, the reaction solution can be warmed above room temperature, such as to 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C. or greater for the incubation.

Following incubation of the reaction solution, in certain example embodiments the DNA-binding particles (that include the cfDNA fragments bound thereto) are separated from the reaction solution, thus forming a particle fraction that includes the DNA-binding particles and a non-particle fraction that does not include the DNA-binding particles. For example, when conventional beads are used as the DNA-binding particles, the beads can be removed by conventional low-speed centrifugation. In certain example embodiments, the pelleted beads can then be washed to remove contaminants. For example, the beads can be washed with an alcoholic solution, such as an alcoholic solution of about 60%, 65%, 70%, 75%, 80%, 85%, or 90% v/v alcohol. In certain examples embodiments, the wash solution can contain a chaotropic salt as described herein. The beads can then be collected via low-speed centrifugation for subsequent elution of the cfDNA fragments from the beads, with the supernatant (non-bead particle fraction) being discarded.

In certain example embodiments, such as when the DNA-binding particles are magnetic beads, the beads can be removed from the reaction solution by subjecting the magnetic beads to a magnetic field and discarding the supernatant (i.e., discarding the non-particle fraction) (e.g., FIG. 2). In certain example embodiments, the collected magnetic beads of the particle fraction can then be washed to remove contaminants. For example, the beads can be washed with an alcoholic solution, such as an alcoholic solution of about 60%, 65%, 70%, 75%, 80%, 85%, or 90% v/v alcohol. In certain examples embodiments, the wash solution can contain a chaotropic salt as described herein. The magnetic beads can then be collected by again subjecting the magnetic beads to a magnetic field and discarding the non-bead component.

Once the DNA-binding particles are separated from the reaction solution, the DNA bound to the DNA-binding particles, including cfDNA fragments, are eluted from the DNA-binding particles of the particle fraction (e.g., FIG. 2). As those skilled in the art will appreciate, any number of elution procedures can be used to elute the bound DNA, depending on the nature of the DNA-binding particles. For example, the bound DNA, including the bound cfDNA fragments, can be eluted via an aqueous buffer such as water and a Tris-EDTA buffer can be used. For example, a Tris buffer of 7, 8, 9, 10, 11, or 12M Tris can be used, with an EDTA concentration of 0.5, 0.6, 0.7, 0.8, 0.9, 0.1, 1.1, 1.2, 1.3, 1.4, or 1.5 mM. In certain examples, the elution buffer can be adjusted to a pH of between 7.0 to 9.0, such as about 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0. In certain example embodiments, the elution buffer is an aqueous that includes 10 mM Tris-HCL+1 mM EDTA, or low TE buffer (10 mM Tris-HCL+0.1 mM EDTA).

In certain example embodiments, column chromatography can be used to enrich large cfDNA fragments as described herein. For example, any DNA-binding particles that bind to DNA, either directly or indirectly, and that are suitable for use in a column can be used to form a column. The biological fluid sample or portion thereof is then added to the column, along with a high concentration alcohol solution and a chaotropic agent, to form a reaction solution as described herein. In certain example embodiments, the DNA-binding particles are beads that are packed together to form a column. In such embodiments, the beads of the column are DNA-binding particles, which—together with the high alcohol solution and the chaotropic agent—result in a reaction solution within the column.

In certain example embodiments, the reaction solution in the column is incubated at one of the times and temperatures described herein for enrichment of large cfDNA fragments. For example, the reaction solution of the column can be incubated for 1, 2, 3, 4, 5, 6, 7, 8, 9, 10, 11, 12, 13, 14, 15, 16, 17, 18, 19, or 20 minutes. Further, the reaction solution of the column can be incubated, for example, at room temperature, such as at about 20° C., 21° C., 22° C., 23° C., 24° C., or 25° C. In other example embodiments, the reaction solution of the column can be warmed above room temperature, such as to 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C. or greater. To obtain the cfDNA, the aqueous components of the reaction solution (i.e., the alcohol solution, the chaotropic agent, and any other aqueous components such as buffers, etc.) are allowed to pass through the column. The DNA, including the cfDNA fragments, can then be eluted from the column as described herein.

In certain example embodiments, a membrane can be used to enrich the large cfDNA as described herein. For example, a biological fluid sample containing DNA can be passed over a silica membrane either via centrifugation or with a vacuum manifold, in the presence of a high alcohol solution and a chaotropic agent. The membrane is then washed with an alcoholic solution and eluted using an aqueous buffer as described herein. For example, the DNA can be eluted using Tris buffer as described herein, such as a Tris-HCL+1 mM EDTA or low TE buffer (10 mM Tris-HCL+0.1 mM EDTA).

By using a high alcohol solution as described herein to enrich cfDNA from a biological sample, cfDNA fragments having a large size can be obtained from the biological sample. For example, using a high alcohol solution as described herein, cfDNA fragments greater than 100 base pairs in length can be eluted from the DNA-binding particles. In certain example embodiments, the elution is enriched with cfDNA fragments greater than about 7,000 base pairs in length, such as cfDNA fragments that are between 7,000 and 12,000 base pairs in length. For example, the enriched cfDNA fragments of about 8,000, 9,000, 10,000, or 11,000 base pairs in length or combinations thereof. In certain example embodiments, the enriched cfDNA fragments are between 10,000 and 11,000 base pairs in length, such as about 10,500 base pairs in length.

In certain example embodiments, the elution obtained from using a high alcohol solution as described herein is additionally enriched with cfDNA fragments having a length of about 150 base pairs, such as cfDNA fragments having a length of about 140, 145, 150, 155, 160, 165, 170, or 175 base pairs in length or combinations thereof. In certain example embodiments, the elution obtained from using a high alcohol solution as described herein is additionally enriched with cfDNA fragments having a length of about 300 base pairs, such as cfDNA fragments having a length of about 280, 285, 290, 295, 300, 305, 310, 315, or 320 base pairs in length or combinations thereof. As those skilled in the art will appreciate, the size of the large cfDNA fragments described herein can be determined by any means known in the art. For example, gel electrophoresis (e.g., agarose gel electrophoresis or polyacrylamide gel electrophoresis) or capillary electrophoresis can be used to determine cfDNA fragment size.

In certain example embodiments, the cfDNA fragments that are enriched according to the methods described herein, including the large cfDNA fragments, are enriched by about 10, 20, 30, 40, 50, 60, 70, 80, 90, or 100% or more as compared to the amount of DNA present in the original sample. In other example embodiments, the cfDNA fragments, including the large cfDNA fragments, are further enriched. For example, the cfDNA fragments may be enriched by 100, 200, 300, 400, 500, 600, 700, 800, 900, or 1000% as compared to the amount of DNA present in the original sample.

Without wishing to be bound by any particular theory, it is believed that the cfDNA fragments enriched using a high alcohol solution and having a length of about 150 base pairs and/or 300 base pairs as described herein are degradation products of the larger DNA fragments, i.e., degradation products of the enriched DNA fragments having a length of about 7,000 and 12,000 base pairs as described herein. For example, and again without being bound by any particular theory, the cfDNA fragments of about 150 base pairs as described herein are typical in size of DNA that is protected by a single octameric nucleosome core. Similarly, the cfDNA fragments of about 150 base pairs as described herein are typical of DNA that is bound (and protected by) a two octameric nucleosome cores.

While the examples described herein rely on a high alcoholic solution to enrich large cfDNA fragments, in certain example embodiments other water miscible solvents can be used to enrich the large cfDNA fragments. Non-limiting examples of water miscible solvents include acetone, acetonitrile, 1,4,-dioxane, dimethylsulfoxide, 1,3-propanediol, tetrahydrofuran, dimethylformamide, dimethoxymethane and diethanolamine.

Enrichment of Small cfDNA from a Biological Sample

In certain example embodiments, serial additions of an alcoholic solution—a first low alcohol solution followed by a second, high alcohol solution—are used to enrich a biological fluid sample with small cfDNA fragments (e.g., FIG. 3). For example, the eluate from one or more of the pretreatment methods described herein is mixed with a low alcohol content first alcoholic solution, one or more first chaotropic agents, and a first mixture of DNA-binding particles to form a first reaction solution having a low alcohol concentration. In certain example embodiments, other components can also be added to the reaction solution, such as detergents, pH buffers, chelators, etc. Yet because of the addition of the low alcohol content alcoholic solution to the mixture, the resultant first reaction solution also has a low alcohol concentration, such as a concentration less than about 35% v/v alcohol. For example, the first reaction solution formed by combining the biological sample eluate, the alcoholic solution, the chaotropic agent, DNA-binding particles, and any other components has an alcohol concentration of 35%, 34%, 33%%, 32%%, 31%, 30%, 29%, 28%, 27%, 26%%, 25%, 24%, 23%, 22%, 21%, 20%, 19%, 18%, 17%, 16%, 15%, 14%, 13%, 12%, 11%, or 10% v/v alcohol.

To achieve a low alcohol concentration for the first reaction solution as described herein, the first alcoholic solution used to form the first reaction solution can be any concentration that—when diluted with the biological sample and other components as described herein—results in the first reaction solution having the low alcohol concentration as described herein. In certain example embodiments, the alcoholic solution used to form the first reaction solution can be added serially, such that the final, first reaction solution has a low alcohol concentration as described herein. Hence, with single or serial additions of the alcoholic solution to form the first reaction solution, the alcohol concentration of the first reaction solution is 35%, 34%, 33%%, 32%%, 31%, 30%, 29%, 28%, 27%, 26%%, 25%, 24%, 23%, 22%, 21, 20%, 19%, 18%, 17%, 16%, 15%, 14%, 13%, 12%, 11%, or 10% v/v alcohol.

With regard to the first chaotropic agent of the first reaction solution, the first chaotropic agent can be any chaotropic agent that favors binding of the cfDNA to the DNA-binding particles. For example, the chaotropic agent can be a chaotropic salt, such as guanidine thiocyanate. In certain example embodiments, such as when the eluate from any pretreatment step contains no chaotropic agent or a lower concentration of chaotropic agent, a higher concentration of the chaotropic agent can be added, along with the other components, to form the first reaction solution. For example, the chaotropic agent that is added to form the reaction solution can be chaotropic salt solution, such as a solution of about 4M, 4.5M, 5M, 5.5M, 6M, 6.5M, 7M, 7.5M or 8M guanidine thiocyanate or other chaotropic agent.

In other example embodiments, such as when the eluate from any pretreatment step is eluted with a chaotropic agent—and therefore the eluate already contains a chaotropic agent—a lower concentration of the chaotropic agent can be added, along with the other components described herein, to form the first reaction solution. For example, the chaotropic agent that is added to form the first reaction solution can be chaotropic salt solution, such as a solution of 0.5M, 1M, 1.5M, 2M, 2.5M, 3M, 3.5M, or 4M guanidine thiocyanate or other chaotropic agent. In certain example embodiments, the final concentration of the chaotropic agent in the first reaction solution is about 2M guanidine thiocyanate, such as 0.5M, 1M, 1.5M, 2M, 2.5M, 3M, 3.5M, or 4M guanidine thiocyanate.

The DNA-binding particles of the first reaction solution can be any type of DNA-binding particles that bind DNA, including cfDNAs, in the presence of alcohol. For example, the DNA-binding particles can be beads. The DNA-binding particles, such as beads, can thus be used to form the first reaction solution having a low alcohol concentration as described herein. In certain example embodiments, the beads can be magnetic beads, such as silica-based magnetic beads, such as magnetic silanol beads. For example, a given amount of the magnetic beads, according to the manufacturer's instructions, can be combined with a solution that includes alcohol and/or a chaotropic agent to form a bead binding solution. The bead binding solution can then be combined with the biological fluid sample—and also combined and/or further adjusted with an alcohol solution, and/or one or more chaotropic agents—to achieve the low-alcohol first reaction solution as described herein (e.g., FIG. 3).

After formation of the first reaction solution, the first reaction solution is incubated for a given amount of time to allow the cfDNA fragments to bind to the DNA-binding particles (e.g., FIG. 3). For example, the reaction solution—which includes, among other components, the biological sample or portion thereof, a chaotropic agent, the DNA-binding particles, and a low concentration of alcohol as described herein—is incubated for 1, 2, 3, 4, 5, 6, 7, 8, 9, 10, 11, 12, 13, 14, 15, 16, 17, 18, 19, or 20 minutes. The reaction solution is incubated, for example, at room temperature, such as at about 20° C., 21° C., 22° C., 23° C., 24° C., or 25° C. In other example embodiments, the reaction solution can be warmed above room temperature, such as to 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C. or greater.

Following incubation of the first reaction solution, in certain example embodiments the DNA-binding particles (that include the cfDNA fragments) are separated from the reaction solution, thus forming a first particle fraction that includes the DNA-binding particles and a first non-particle fraction that does not include the DNA-binding particles. For example, and as those skilled in the art will appreciate, when conventional beads are used as the DNA-binding particles, the beads can be removed from the first reaction solution by conventional low-speed centrifugation. In certain example embodiments, such as when the DNA-binding particles are magnetic beads, the beads are removed from the first reaction solution by subjecting the magnetic beads to a magnetic field.

After removal of the DNA-binding particles from the first reaction solution, and when enriching small cfDNA fragments with serial alcohol additions as described herein, a second reaction solution is formed having a high alcohol concentration (e.g., FIG. 3). For example, the first non-particle fraction is contacted with a second alcoholic solution having a high concentration of alcohol, a second mixture of DNA-binding particles, and, in certain examples, a second chaotropic agent to form a second reaction solution. In certain example embodiments, other components can also be added to the second reaction solution, such as detergents, pH buffers, chelators, etc. Yet because of the addition of the high alcohol content second alcoholic solution to the mixture, the resultant reaction solution also has a high alcohol concentration, such as a concentration above 45% v/v alcohol. For example, the second reaction solution formed by combining the non-particle faction, the second alcoholic solution, the second chaotropic agent, a second mixture of DNA-binding particles, and any other components has an alcohol concentration of 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75% alcohol v/v.

In certain example embodiments, to achieve a high alcohol concentration for the second reaction solution, the concentration of the alcohol solution used to form the second reaction solution is high. For example, the second alcohol solution that is used to form the second reaction solution can be about 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, or 65% v/v alcohol.

In certain example embodiments, to achieve the high alcohol concentration of the second reaction solution, serial dilutions with an alcohol solution can be used. For example, the non-particle fraction can be contacted with an initial alcohol solution of 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, or 65% v/v alcohol. Thereafter, a second and/or subsequent alcohol solution of 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, or 65% v/v alcohol can be added. Regardless, with single or serial additions of alcohol, in certain example embodiments the second reaction solution has an alcohol concentration of 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75% alcohol v/v.

In certain example embodiments, a second chaotropic agent can be added to the second reaction mixture. Because the non-particle fraction already contains, among other components, the first chaotropic agent in certain example embodiments, adding the second chaotropic agent can be optional. When added, the second chaotropic agent can be any chaotropic agent that favors binding of the cfDNA to the DNA-binding particles. For example, the chaotropic agent can be a chaotropic salt, such as guanidine thiocyanate. In certain example embodiments, the chaotropic agent that is added to form the reaction solution can be chaotropic salt solution, such as a solution of about 4M, 4.5M, 5M, 5.5M, 6M, 6.5M, 7M, 7.5M or 8M guanidine thiocyanate or other chaotropic agent. In other example embodiments, the chaotropic agent that is added to form the reaction solution can be chaotropic salt solution, such as a solution of 0.5M, 1M, 1.5M, 2M, 2.5M, 3M, 3.5M, or 4M guanidine thiocyanate or other chaotropic agent. In certain example embodiments, the final concentration of the chaotropic agent in the second reaction solution is about 2M guanidine thiocyanate, such as 0.5M, 1M, 1.5M, 2M, 2.5M, 3M, 3.5M, or 4M guanidine thiocyanate.

The second mixture of DNA-binding particles of the second reaction solution can be any type of DNA-binding particles that bind DNA, such as cfDNAs, in the presence of alcohol. For example, the DNA-binding particles can be beads. The DNA-binding particles, such as beads, can thus be used to form the reaction solution having a high alcohol concentration as described herein. In certain example embodiments, the beads can be magnetic beads, such as silica-based magnetic beads, such as magnetic silanol beads. For example, a given amount of the magnetic beads, according to the manufacturer's instructions, can be combined with a solution that includes alcohol and/or a chaotropic agent to form a bead binding solution. The bead binding solution can then be combined with the biological fluid sample—and also combined and/or further adjusted with an alcohol solution, and/or one or more chaotropic agents—to achieve the high-alcohol reaction solution as described herein (e.g., FIG. 3).

To enrich small cfDNA fragments from the biological fluid sample, the second reaction solution is incubated for a given amount of time to allow the cfDNA fragments to bind to the second mixture of DNA-binding particles (e.g., FIG. 3). For example, the second reaction solution—which includes, among other components, the non-particle fraction (or portion thereof), an optional chaotropic agent, the second DNA-binding particles, and a high concentration of alcohol as described herein—is incubated for 1, 2, 3, 4, 5, 6, 7, 8, 9, 10, 11, 12, 13, 14, 15, 16, 17, 18, 19, or 20 minutes. Further, the second reaction solution is incubated, for example, at room temperature, such as at about 20° C., 21° C., 22° C., 23° C., 24° C., or 25° C. In other example embodiments, the second reaction solution can be warmed above room temperature, such as to 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C. or greater for the incubation.

Following incubation of the second reaction solution, in certain example embodiments the second mixture of DNA-binding particles (that include the small cfDNA fragments) are separated from the reaction solution, thus forming a second particle fraction that includes the DNA-binding particles and a second non-particle fraction that does not include the DNA-binding particles. For example, when conventional beads are used as the DNA-binding particles, the beads can be removed by conventional low-speed centrifugation. In certain example embodiments, the pelleted beads can then be washed to remove contaminants. For example, the beads can be washed with an alcoholic solution, such as an alcoholic solution of about 60%, 65%, 70%, 75%, 80%, 85%, or 90% v/v alcohol. In certain examples embodiments, the wash solution can contain a chaotropic salt. The beads can then be collected via centrifugation for subsequent elution, with the supernatant (non-bead particle fraction) being discarded.

In certain example embodiments, such as when the second mixture of DNA-binding particles are magnetic beads, the beads can be removed from the reaction solution by subjecting the magnetic beads to a magnetic field and discarding the supernatant (i.e., discarding the second non-particle fraction) (e.g., FIG. 3). In certain example embodiments, the collected magnetic beads of the second particle fraction can then be washed to remove contaminants. For example, the beads can be washed with an alcoholic solution, such as an alcoholic solution of about 60%, 65%, 70%, 75%, 80%, 85%, or 90% v/v alcohol. In certain examples embodiments, the wash solution can contain a chaotropic salt. The magnetic beads can then be collected by again subjecting the magnetic beads to a magnetic field and discarding the non-bead component.

Once the second mixture of DNA-binding particles are separated from the reaction solution, the DNA bound to the second mixture of DNA-binding particles, including cfDNA fragments, are eluted from the DNA-binding particles of the particle fraction (e.g., FIG. 3). As those skilled in the art will appreciate, a number of elution procedures can be used to elute DNA bound to the second mixture of DNA-binding particles, depending on the nature of the DNA-binding particles. For example, a Tris buffer of 7, 8, 9, 10, 11, or 12M Tris can be used, with an EDTA concentration of 0.5, 0.6, 0.7, 0.8, 0.9, 0.1, 1.1, 1.2, 1.3, 1.4, or 1.5 mM. In certain examples, the elution buffer can be adjusted to a pH of between 7.0 to 9.0, such as about 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0. In certain example embodiments, the elution buffer is an aqueous that includes 10 mM Tris-HCL+1 mM EDTA, or low TE buffer (10 mM Tris-HCL+0.1 mM EDTA).

In certain example embodiments, column chromatography can be used to enrich the small cfDNA fragments as described herein. For example, any DNA-binding particles that bind to DNA, either directly or indirectly—and that are suitable for use in a column—can be used to form a column. The biological fluid sample or portion thereof is then added to the column, along with a low concentration alcohol solution and a first chaotropic agent, to form a first reaction solution (within the column) as described herein. The eluate can then be collected, and thereafter subjected to column chromatography using a high alcoholic solution has described herein.

In certain example embodiments, the DNA-binding particles of the first reaction solution and/or the second reaction solution are beads, such as silica-based beads, that are packed together to form a column. In such embodiments, the beads of the column are the DNA-binding particles, which—together with the alcohol solutions and the chaotropic agents—result in a first reaction solution within the column and/or a second reaction solution within the column. In certain example embodiments, the first reaction solution and/or the second reaction solution of the column is incubated at one of the times and temperatures described herein. For example, the first reaction solution and/or the second reaction solution of the column can be incubated for 1, 2, 3, 4, 5, 6, 7, 8, 9, 10, 11, 12, 13, 14, 15, 16, 17, 18, 19, or 20 minutes. Further, the first reaction solution and/or the second reaction solution of the column can be incubated, for example, at room temperature, such as at about 20° C., 21° C., 22° C., 23° C., 24° C., or 25° C. In other example embodiments, the first reaction solution and/or the second reaction solution of the column can be warmed above room temperature, such as to 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C. or greater.

To obtain the small cfDNA fragments using a column, the aqueous components of the first reaction solution (i.e., the low alcohol solution, the chaotropic agent, and any other aqueous components such as buffers, etc.) are allowed to pass through the column. The aqueous component is then contacted with the high-alcohol solution to form the second reaction solution. The DNA, including the small cfDNA fragments, can then be eluted from the second column as described herein. That is, the small cfDNA fragments are eluted from the DNA-binding particles, such the beads, from the column.

In other example embodiments, a membrane can be used to enrich the small cfDNA as described herein. For example, a biological fluid sample containing DNA can be passed over a silica membrane either via centrifugation or with a vacuum manifold, in the presence of a low alcohol solution and a chaotropic agent. The flow-through or supernatant is then passed over a silica membrane either via centrifugation or with a vacuum manifold, in the presence of a high alcohol solution and a chaotropic agent. The membrane is then washed with an alcoholic solution and eluted using an aqueous buffer as described herein. For example, the DNA can be eluted using Tris buffer as described herein, such as a Tris-HCL+1 mM EDTA or low TE buffer (10 mM Tris-HCL+0.1 mM EDTA).

By using a low alcohol solution followed by a high alcohol solution as described herein to enrich cfDNA from a biological sample, cfDNA fragments having a small size can be obtained from the biological sample. For example, the eluate resulting from the biological sample using serial alcohol additions is enriched with cfDNA fragments that are less than about 100 base pairs, such as cfDNA fragments that are about 10, 15, 20, 25, 30, 35, 40, 45, 50, 55, 60, 65, 70, 75, 80, 85, 90, or 95 base pairs in length or combinations thereof. In certain examples, the eluate is enriched with cfDNA fragments of roughly 30 base pairs in length, such as cfDNA fragments that are 25, 26, 27, 28, 29, 30, 31, 32, 33, 34, or 35 base pairs in length. As those skilled in the art will appreciate, the size of the small cfDNA fragments described herein can be determined by any means known in the art. For example, gel electrophoresis (e.g., agarose gel electrophoresis or polyacrylamide gel electrophoresis) or capillary electrophoresis can be used to determine cfDNA fragment size.

In certain example embodiments, the cfDNA fragments that are enriched according to the methods described herein, including the small cfDNA fragments, are enriched by about 10, 20, 30, 40, 50, 60, 70, 80, 90, or 100% or more as compared to the amount of DNA present in the original sample. In other example embodiments, the cfDNA fragments, including the small cfDNA fragments, are further enriched. For example, the cfDNA fragments may be enriched by 100, 200, 300, 400, 500, 600, 700, 800, 900, or 1000% as compared to the amount of DNA present in the original sample.

While the methods of using a low alcoholic solution followed by a high alcoholic solution can be used to enrich small cfDNA fragments from a biological sample as described herein, in certain example embodiments cfDNA fragments can additionally or alternatively be eluted from the first particle fraction that is removed from the first reaction solution. For example, once the first particle fraction is removed from the low-alcohol first reaction solution—and as those skilled in the art will appreciate—any number of elution procedures can be used to elute DNA bound to the DNA-binding particles of the first particle fraction, depending on the nature of the DNA-binding particles. For example, when beads including carboxylic acid groups are used for DNA binding, the bound DNA, including the bound cfDNA fragments, can be eluted with an aqueous buffer, such as water or Tris-EDTA as described herein. In other example embodiments, such as when silica-based beads are used, a Tris-EDTA buffer can be used. For example, a Tris buffer of 7, 8, 9, 10, 11, or 12M can be used, with an EDTA concentration of 0.5, 0.6, 0.7, 0.8, 0.9, 0.1, 1.1, 1.2, 1.3, 1.4, or 1.5 mM. In certain examples, the elution buffer can be adjusted to a pH of between 7.0 to 9.0, such as about 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0.

In certain example embodiments, the cfDNA fragments eluted from the DNA-binding particles of the first particle fraction are large, for example, such as approximately 2,000 to 10,000 base pairs in length. For example, the cfDNA fragments eluted from the DNA-binding particles of the first particle fraction can be approximately 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, or 10,500 base pairs in length or combinations thereof.

While the examples described herein rely on a low alcoholic solution and thereafter a high alcoholic solution to enrich small cfDNA fragments, in certain example embodiments other water miscible solvents can be used to enrich the small cfDNA fragments. Non-limiting examples of water miscible solvents include acetone, acetonitrile, 1,4,-dioxane, dimethylsulfoxide, 1,3-propanediol, tetrahydrofuran, dimethylformamide, dimethoxymethane and diethanolamine.

Compositions & Kits for Enrichment of cfDNA from a Biological Sample

In certain example embodiments, provided are compositions for enriching cfDNA fragments from a biological fluid sample. Generally, the compositions include an alcoholic solution, such as a high-alcohol or low alcohol solution, a chaotropic agent, and a plurality of DNA-binding particles. In certain example embodiments, the composition can also include other components, such as detergents, pH buffers, chelators, etc., that can be added to stabilize the composition.

With regard to the chaotropic agent of the composition, the chaotropic agent can be any chaotropic agent that, when contacted with a biological sample containing DNA, favors binding of the cfDNA fragments to the DNA-binding particles of the composition. For example, the chaotropic agent can be a chaotropic salt, such as guanidine thiocyanate. In certain example embodiments, such as when the eluate from any pretreatment step contains no chaotropic agent or a lower concentration of chaotropic agent, the composition can include a higher concentration of the chaotropic agent. For example, the chaotropic agent of the composition can be chaotropic salt solution, such as a solution of about 4M, 4.5M, 5M, 5.5M, 6M, 6.5M, 7M, 7.5M or 8M guanidine thiocyanate or other chaotropic agent.

In other example embodiments, such as when the eluate from any pretreatment step is eluted with a chaotropic agent—and therefore the eluate already contains a chaotropic agent—the composition can include a lower concentration of the chaotropic agent. For example, the chaotropic agent of the composition can be 0.5M, 1M, 1.5M, 2M, 2.5M, 3M, 3.5M, or 4M guanidine thiocyanate or other chaotropic agent. In certain example embodiments, the concentration of the chaotropic agent in the composition can be adjusted such that, when the composition is mixed with a portion of the biological fluid sample, the mixture (i.e., the reaction solution) has a concentration of the chaotropic agent of about 2M guanidine thiocyanate, such as 0.5M, 1M, 1.5M, 2M, 2.5M, 3M, 3.5M, or 4M guanidine thiocyanate.

The DNA-binding particles of the composition can be any type of DNA-binding particles that bind DNA, including cfDNAs, in the presence of alcohol. For example, the DNA-binding particles of the composition can be beads, such as silica beads. In certain example embodiments, the beads can be magnetic beads, such as silica-based magnetic beads (e.g., magnetic silanol beads). When mixed with a biological fluid sample according to the methods described herein, for example, such magnetic beads can be easily removed from the reaction solution by subjecting the silica-based magnetic beads to a magnetic field.

In certain example embodiments, the composition is a high-alcohol composition. For example, the alcohol concentration of the high-alcohol composition can be greater than about 60% v/v alcohol, such as about 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, or 65% v/v alcohol. Hence, in certain example embodiments, the concentration of alcohol in the composition can be adjusted such that, when the composition is mixed with a biological fluid sample or portion thereof, the concentration of the alcohol in the resultant reaction solution is greater than 45% v/v alcohol, such as about 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75% alcohol v/v.

The high-alcohol compositions can be used, for example, to enrich large cfDNA fragments from a biological fluid sample according to the methods described herein. For example, the high-alcohol composition can be mixed with a biological fluid sample or portion thereof to form a reaction solution as described herein. The reaction solution is then incubated according the methods described herein, and—upon removal of the DNA-binding particles—large cfDNA fragments can be eluted from DNA-binding particles according to the methods described herein.

In certain example embodiments, the composition is a low-alcohol composition. For example, the composition can contain 40% v/v alcohol or less, such as about 35%, 30%, 25%, or 20% alcohol v/v. In other example embodiments, the alcohol solution can be higher, such that dilution of the composition with the biological sample or portion thereof results in a first reaction solution. In certain example embodiments, the low-alcohol composition can be used, according to the methods described herein, to form the first reaction solution in the enrichment of small cfDNA fragments. For example, the low-alcohol composition can be mixed a biological sample or portion thereof according to the methods described herein, such that the alcohol of the resultant first reaction solution is about 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, or 10% v/v alcohol. Following incubation of the first reaction solution according to the methods described herein, the non-particle fraction can be mixed with the high-alcohol composition according to the methods described herein to form a second reaction solution. Small cfDNA fragments can then be enriched from the particle fraction of the second reaction solution, according to the methods described herein.

In certain example embodiments, provided are kits for enriching cfDNA fragments from a biological sample. In one example embodiment, the kit includes the high-alcohol composition described herein, along with instructions for using the high-alcohol composition to enrich large cfDNA fragments from a biological fluid sample. In other example embodiments, provided is a kit for enriching small cfDNA fragments from a biological sample. The kit for enriching small cfDNA fragments includes, for example, the low-alcohol composition and separately the high-alcohol composition as described herein. The kit for enriching small cfDNA fragments also includes instructions for using the low alcohol composition, followed by the high-alcohol composition, to enrich the small cfDNA fragments according the methods described herein.

While the example compositions and kits described herein rely on alcohol, in certain example embodiments the compositions and/or kits including the compositions can include other water miscible solvents that can be used to enrich the small or large cfDNA fragments. Non-limiting examples of water miscible solvents include acetone, acetonitrile, 1,4,-dioxane, dimethylsulfoxide, 1,3-propanediol, tetrahydrofuran, dimethylformamide, dimethoxymethane and diethanolamine.

Example Applications

As those skilled in the art will appreciate based on the present disclosure, the methods and compositions described herein can be used in a variety of cfDNA-related applications. Such methods and compositions are particularly useful, for example, when cfDNA fragments are scarce in a biological sample, such as in a urine sample, inasmuch as the methods and compositions described herein can be used to enrich cfDNA fragments in the sample, thereby providing sufficient cfDNA quantitates for testing an analysis. The enriched cfDNA fragments can then be used in any medical application, for example, in which analyzing cfDNA is useful. This includes the analysis of cfDNA fragments for treatment and diagnostic applications related to oncological screening, infectious diseases, renal disorders, pre-natal/fetal monitoring and testing, and other applications.

In certain example embodiments, the methods and compositions described herein can be used for systemic treatments and diagnostics, i.e., diagnostics associated with identifying a disease state anywhere within a subject. For example, the cfDNA fragments enriched from a biological sample as described herein can be screened for the presence or absence of a genetic marker associated with a genetic condition or disease in the subject, thus aiding in the diagnosis of a genetic condition or disease in the subject from which the sample was collected. In certain example embodiments, the cfDNA fragments enriched from a biological sample as described herein can be used to for oncological screening. For example, cfDNA fragments originating from a lung tumor in a subject can contain genetic markers identifying the tumor as a lung tumor. When the subject's urine or blood, for example, is collected—and enriched for cfDNA fragments according to the methods described herein—the enriched cfDNA can be screened for the lung tumor marker. The presence of the marker, for example, provides an indication that the subject has a lung tumor.

In certain example embodiments, the cfDNA fragments enriched from a biological sample as described herein can be screened for the presence or absence of a nucleic acids associated with a pathogen, thus allowing detection of an infectious agent within a subject. For example, when analyzing a urine or blood sample from a subject, the presence of a marker associated with a cfDNA fragment of a bacterium can indicate that the subject is infected with the bacterium.

In certain example embodiments, the cfDNA fragments enriched from a biological sample as described herein can be used for fetal testing, such as by detecting the presence or absence of a genetic marker associated with a genetic condition or disease state in a fetus. For example, a blood or urine sample can be collected from a pregnant mother (i.e., the fetal host). The sample or portion thereof can then be enriched with cfDNA fragments as described herein, the cfDNA fragments including those that originate from the fetus but that are present in the mother's blood and/or urine. The enriched cfDNA fragments can then be screened for genetic markers associated with a fetal genetic condition or disease state.

In certain example embodiments, the methods and compositions described herein can be used for urinary-tract-specific treatment and diagnostics. Because of the large size of the cfDNA fragments that are enriched from a urine using high levels of alcohol as described herein, it is believed that such larger cfDNA fragments predominately originate from within the urinary tract system. As discussed previously, and without being bound by any particular theory, the effective pore of the urinary tract glomerular filtration barrier is around 8 nm, and the membranes of the barrier are generally negatively charged. Hence, cfDNA fragments of larger sizes circulating in the blood plasma are not believed to pass through the glomerular pore—at least to any significant extent. Hence, it is believed that the large cfDNA fragments that are enriched from urine using high levels of alcohol as described herein are predominantly post-glomerular cfDNA fragments, meaning that such cfDNA fragments arise from DNA that exists between the glomerular barrier to where urine exits at the urethra. For example, the cfDNA fragments enriched from urine using high levels of alcohol as described herein arise from cells of the glomerular capsule, the nephron tubule, the collecting duct, the ureter, the bladder, the urethra, and/or a host of other urinary tract structures having various cell types within the urinary tract.

Conversely, and again without being bound by any particular theory, it is believed that the small cfDNA fragments described herein are of a size that can pass through the glomerular pore. Hence, such small cfDNA fragments—when enriched from a urine sample, for example—are believed to include cfDNA circulating within the subject's blood, as well as any cfDNA fragments arising within the urinary tract system. That is, the small cfDNA fragments enriched from a urine sample are not believed to be confined to arising from within the urinary tract, as compared to the large cfDNA fragments that are enriched as described herein from a urine sample (and which are believed to originate within the urinary tract). As such, the small cfDNA fragments may be particularly useful for systemic diagnostics and treatments.

Because it is believed that large cfDNA fragments enriched from a urine sample are originate within the urinary tract, it is further believed that enrichment of large cfDNA fragments from a urine sample, as described herein, can be used in conjunction with treatment and diagnostics of disease conditions arising within the urinary tract. For example, a sample of urine is collected from a subject, and large cfDNA fragments are enriched from the sample as described herein. The large cfDNA fragments can then, for example, be screened for genetic markers of various disease states as described herein. For example, the large cfDNA fragments can be screened for genetic markers of pathogens, the presence of which can indicate the presence of the pathogen within the urinary tract system. In certain example embodiments, the enriched large cfDNA fragments from a urine sample can be screened for a variety of cancer markers, including those cancers that can originate outside the urinary tract. The presence or absence of a particular marker, as determined from the cfDNA fragments of a urine sample, however, can indicate the presence of a primary or secondary cancer within the urinary tract. Notably, screening enriched cfDNA fragments from a blood sample, for example, can miss such urinary tract disease states or conditions, as many cfDNA fragments originating in the urinary tract can be excreted in the urine without being present in any significant levels in the blood. Additionally or alternatively, enrichment of large cfDNA fragments from a non-urine sample, such as from a blood sample, can be used for systemic diagnostic and treatment applications.

EXAMPLES

The present invention is described in further detail in the following examples, which are not in any way intended to limit the scope of the invention as claimed. The attached Figures are meant to be considered as integral parts of the specification and description of the invention. All references cited are herein specifically incorporated by reference for all that is described therein. The following examples are offered to illustrate, but not to limit, the claimed invention.

Example 1

Pretreatment of Biological Sample for cfDNA Enrichment

This example describes the use sample centrifugation and chromatography to clear a urine sample of cellular debris, proteins, small molecules, and other impurities, in accordance with certain example embodiments. The centrifugation and chromatography also help reduce the urine volume (and hence concentrate the cfDNA) to a more manageable volume for downstream silica-bead-based purification (see Examples 2 and 3).

More particularly, voided urine was collected in a specimen container, to which EGTA (final concentration of 5 mM) and a preservative (Streck Cell Preservative™) was added and mixed for approximately 1.0 min. The mixture was then centrifuged twice to remove any large cellular material and debris. The resultant supernatant, containing the cell free DNA, was then concentrated/purified via anion exchange chromatography using DEAE Sepharose (see FIG. 1).

For the chromatography, 2 mL of DEAE Sepharose resin slurry (GE Healthcare) was dispensed into a disposable chromatography column (BioRad™). The resin bed was washed with 10 mL of low TE buffer to yield a final bed volume of 1 mL. Then ~50-250 mL of centrifuged urine was applied to the DEAE sepharose resin bed and the flow-through was discarded. The cfDNA bound resin was washed with 10 mL of low TE buffer and subsequently eluted with 3 mL of 6M chaotropic salt (e.g., guanidine thiocyanate or guanidine HCl).

Notably, "batch" binding to anion exchange resin and column-based purification provide similar results and hence can be used interchangeably. For example, washed DEAE Sepharose resin is resuspended with ~50-250 mL of centrifuged urine and incubated for ~1 hr to bind cfDNA fragments. The resulting mixture is then centrifuged to collect the resin, and the supernatant is discarded. The cfDNA bound resin is then washed with low TE buffer, centrifuged again, and then eluted with 6M chaotropic salt.

Example 2

Enrichment of Large cfDNA

This example, which is summarized generally in FIG. 2, describes the enrichment of large cfDNA from a urine sample.

Briefly, the eluate from Example 1 was further purified by adding 4 volumes of bead binding solution (i.e., 100 mM Tris pH8, 2.5M guanidine thiocyanate, 10% Triton, 40% isopropanol, and 2 mg magnetic silica beads) and 3 volumes of 100% isopropanol to one volume of the elution from Example 1. The final composition of the DNA-containing sample is 50 mM Tris pH8, 2M guanidine thiocyanate, 5% Triton, and 57% isopropanol. The magnetic silica beads can be purchased, for example, as Dynabeads™ MyOne™ Silane beads, ThermoFisher™.

Once the bead binding solution is added to the elution, the resulting reaction solution mixture was incubated at room temperature for 10 min to allow time for the DNA in the mixture to bind to the magnetic silica beads. The mixture was then placed on a magnetic rack to separate the DNA-containing beads from supernatant, according to the manufacturer's instructions. The supernatant was removed from the sample and the bound DNA was eluted from the magnetic silica beads with an aqueous elution solution (i.e., water, low TE [10 mM Tris, pH 8.0, and 0.1 mM EDTA etc.]) (FIG. 2). The eluted DNA has sizes of ~160 bp, ~300 bp, and high molecular weight gDNA (>5 kbp) (see Example 4).

Example 3

Enrichment of Small cfDNA

This example, which is summarized generally in FIG. 3, describes the enrichment of small cfDNA from a urine sample.

More particularly, this example shows that cfDNA can be size selected to decrease the amount of high molecular weight genomic DNA and to enrich for smaller DNA species of 20-60 bp. As in Example 2, approximately 4 volumes of bead binding solution (100 mM Tris pH8, 2.5M guanidine thiocyanate, 10% Triton, 40% isopropanol, magnetic silica beads) was added to one volume of eluate from Example 1, such that the final composition of the DNA containing buffer is 80 mM Tris pH8, 3.2M guanidine thiocyanate, 8% Triton, 30% isopropanol. The reduced isopropanol concentration of this solution, as compared to the bead binding solution of Example 2, is believed to favor binding of larger DNA fragments to the magnetic silica beads relative to binding of smaller DNA species.

Following addition of the bead binding solution, the sample was incubated at room temperature for 10 min to allow the larger DNA species to bind to the magnetic silica beads, while smaller molecular weight DNA remains in the supernatant. After placing the sample on a magnetic rack, the supernatant is transferred to a new tube (FIG. 3), to which additional magnetic silica beads and 3 volumes of 100% isopropanol are added, such that the final composition of the resultant solution was 50 mM Tris pH8, 2M guanidine thiocyanate, 5% Triton, 57% isopropanol. This mixture was then incubated at room temperature for 10 min to allow the remaining small DNA species to bind to the magnetic silica beads, and subsequently placed on a magnetic rack to separate DNA-containing beads from supernatant. The supernatant was removed and the DNA was eluted from silica beads (FIG. 3) with low TE (10 mM Tris-HCL+0.1 mM EDTA). Purifying DNA in this way yields size-selected cfDNA with sizes of 20-60 bp and vastly reduced amounts of high molecular weight gDNA (>5 kbp), as compared to Example 2 (see Example 4).

Example 4

Determination of cfDNA Fragment Size

This example describes the determination of DNA fragment size of the DNA in samples enriched by the methods described in Examples 1-3.

Briefly, approximately 1.0 ng of the purified DNA from Examples 1 and 2 was run on an Agilent Bioanalyzer high-sensitivity chip according to the manufacturer's instructions with the inclusion of both low (35 base pairs) and high (~10,000 base pairs) size markers used for normalization.

Figure 4:
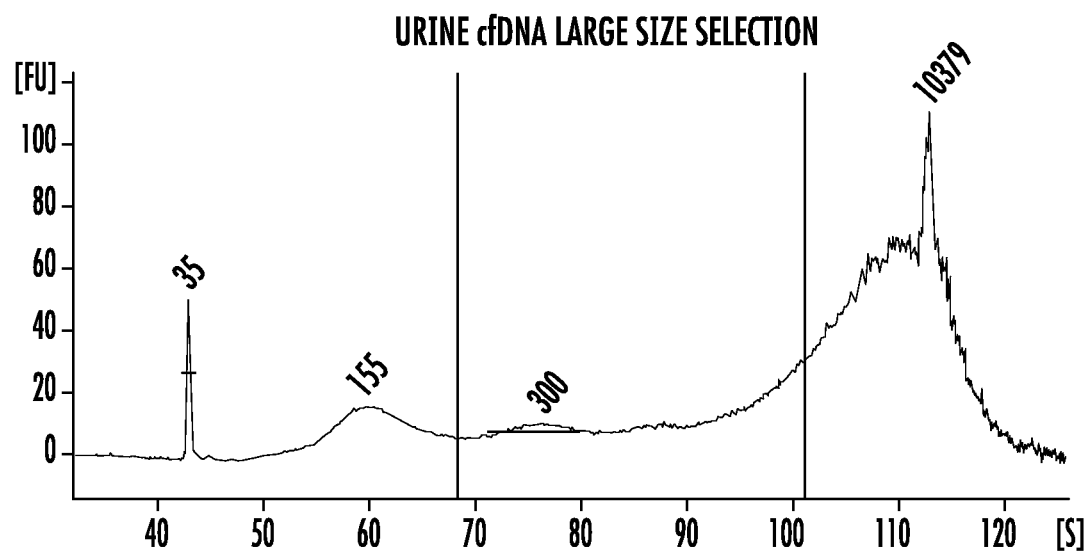
FIG. 4 is a graph showing the enrichment of large cfDNA fragments from a urine sample, in accordance with certain example embodiments. The x-axis indicates electrophoresis time (s), while the y-axis shows the fluorescence intensity (FU). DNA marker peaks at 35 base pairs and 10380 base pairs are shown, with the large cfDNA fraction located near the larger marker.

As shown in FIG. 4, enriching DNA as described above and with reference to FIG. 1 and FIG. 2 (Examples 1 and 2) yields cfDNA with sizes of ~160 bp, ~300 bp, and high molecular weight gDNA (>5 kbp). Also, the x-axis indicates electrophoresis time (s), while the y-axis the fluorescence intensity (FU) (FIG. 4). Sizes of DNA markers used for size estimation are indicated as sharp peaks at 35 bp and 10379 bp (FIG. 4). The sizes of enriched DNA species are indicated in based pairs ("bp") above the peaks of interest (FIG. 4). The large molecular genomic DNA species (100s+ in electrophoresis time) overlaps with the sharp marker peak at 10,379 bp.

Figure 5:
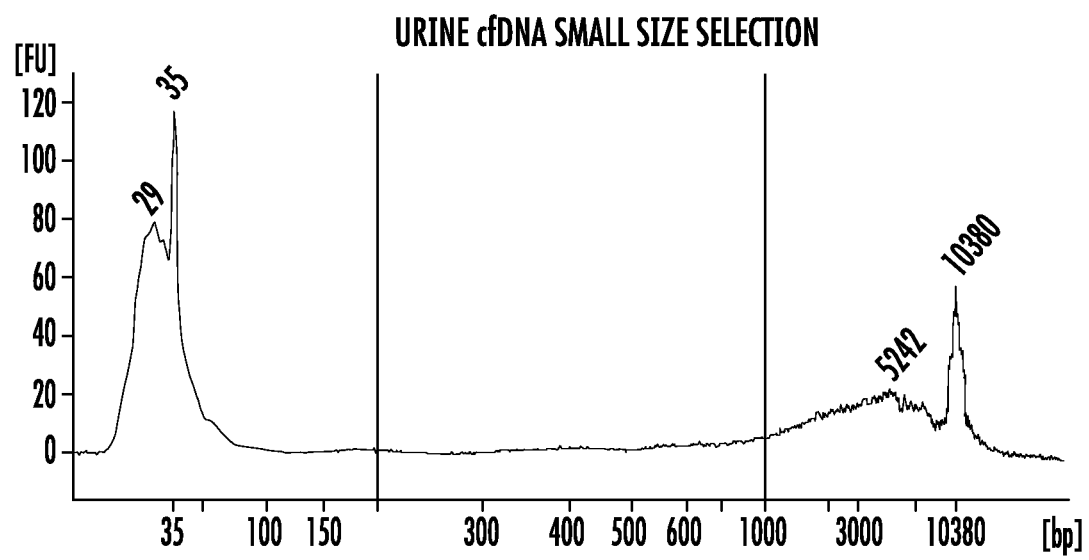
FIG. 5 is a graph showing the enrichment of small cfDNA fragments from a urine sample, in accordance with certain example embodiments. The x-axis indicates electrophoresis time (s), while the y-axis the fluorescence intensity (FU). DNA marker peaks at 35 base pairs and 10380 base pairs are shown, with the small cfDNA fraction located near the 35-base-pair marker.

As shown in FIG. 5, enriching DNA as described above and with reference to FIG. 1 and FIG. 3 (Examples 1 and 3) yields cfDNA with sizes of 20-60 bp. Like with FIG. 4, the x-axis indicates electrophoresis time (s), while the y-axis the fluorescence intensity (FU) (FIG. 5). Sizes of DNA markers used for size estimation are indicated as sharp peaks at 35 bp and 10379 bp (FIG. 5). The sizes of enriched DNA species are indicated in based pairs ("bp") above the peaks of interest (FIG. 5). Due to the sometimes abundant quantity of large genomic DNA fragments, in some cases this species will co-purify with the small DNA fraction (see FIG. 5, peak around 5200 bp).

We claim:

1. A method for enriching systemic cell-free DNA (cfDNA) fragments from a urine sample, comprising:
   contacting a urine sample with a first alcoholic solution, a first chaotropic agent, and a first plurality of DNA-binding particles to form a first reaction solution, wherein the first reaction solution has an alcohol concentration of 35% v/v or less;

separating the first plurality of DNA-binding particles from the first reaction solution, thereby forming a first particle fraction and a first non-particle fraction, wherein the first particle fraction comprises post-glomerular cfDNA fragments;

contacting the first non-particle fraction with a second alcoholic solution and a second plurality of DNA-binding particles to form a second reaction solution, wherein the second reaction solution has an alcohol concentration of at least 55% v/v alcohol;

separating the second plurality of DNA-binding particles from the second reaction solution, thereby forming a second particle fraction and a second non-particle fraction; and eluting cfDNA fragments from the second plurality of DNA-binding particles of the particle fraction, wherein the eluate is enriched with systemic cfDNA fragments having a length of between about 10 base pairs and 80 base pairs.

2. The method of claim 1, wherein the first plurality of DNA-binding particles are silica magnetic bead particles and wherein separating the first plurality of silica magnetic bead particles from the first reaction solution comprises subjecting the first reaction solution to a magnetic field.

3. The method of claim 2, wherein the second plurality of DNA-binding particles are silica magnetic bead particles and wherein separating the second plurality of silica magnetic bead particles from the second reaction solution comprises subjecting the second reaction solution to a magnetic field.

4. The method of claim 1, wherein the eluate is enriched with cfDNA fragments of about 30 base pairs.

5. The method of claim 1, wherein the alcohol of the first reaction solution or the second reaction solution is isopropyl alcohol or ethyl alcohol.

6. The method of claim 1, further comprising contacting the urine sample with a chelating agent before forming the first reaction solution.

7. The method of claim 6, wherein the chelating agent is ethylenediaminetetraacetic acid (EDTA), ethylene glycol-bis(P-aminoethyl ether)-N,N,N',N'-tetraacetic acid (EGTA), or a combination thereof.

8. The method of claim 1, further comprising, before forming the first reaction solution, subjecting the urine sample to centrifugation, wherein the centrifugation results in a supernatant that is substantially free of whole cells.

9. The method of claim 8, wherein contacting the urine sample to form the first reaction solution comprises contacting the supernatant that is substantially free of whole cells.

10. The method of claim 8, further comprising reducing the volume of the supernatant by subjecting the supernatant to ion-exchange chromatography.

11. The method of claim 10, wherein the volume of the supernatant is reduced to 20 ml or less.

12. The method of claim 10, wherein the ion-exchange chromatography substantially removes cellular debris from the supernatant, the cellular debris comprising proteins, lipids, subcellular organelles, or combinations thereof.

13. The method of claim 1, wherein the chaotropic agent is a salt.

14. The method of claim 1, wherein the chaotropic agent is guanidine thiocyanate and wherein the first reaction solution has a guanidine thiocyanate concentration of at least 2 M guanidine thiocyanate.

15. The method of claim 1, wherein the chaotropic agent is guanidine thiocyanate and wherein the second reaction solution has a guanidine thiocyanate concentration of at least 2 M guanidine thiocyanate.

16. The method of claim 1, wherein the eluate is enriched with cfDNA fragments having a length of between about 20 base pairs and 60 base pairs.

17. The method of claim 1, wherein the eluate is substantially free of DNA greater than 5,000 base pairs in length.

18. The method of claim 1, wherein the alcohol concentration of the first reaction solution is 25% to 35% v/v.

19. The method of claim 1, wherein the alcohol concentration of the second reaction solution is 55% to 60% v/v.

* * * * *